United States Patent
Nakagawa et al.

(10) Patent No.: US 10,573,007 B2
(45) Date of Patent: Feb. 25, 2020

(54) IMAGE PROCESSING APPARATUS, IMAGE PROCESSING METHOD, AND IMAGE PROCESSING PROGRAM

(71) Applicants: KOWA COMPANY, LTD., Nagoya-shi, Aichi (JP); Casio Computer Co., Ltd., Shibuya-ku, Tokyo (JP)

(72) Inventors: Toshiaki Nakagawa, Higashimurayama (JP); Takao Shinohara, Higashimurayama (JP); Yasushi Maeno, Hamura (JP); Akira Hamada, Hamura (JP)

(73) Assignees: KOWA COMPANY, LTD. (JP); CASIO COMPUTER CO., LTD.

( * ) Notice: Subject to any disclaimer, the term of this patent is extended or adjusted under 35 U.S.C. 154(b) by 0 days.

(21) Appl. No.: 15/752,946

(22) PCT Filed: Aug. 9, 2016

(86) PCT No.: PCT/JP2016/073496
§ 371 (c)(1),
(2) Date: Feb. 15, 2018

(87) PCT Pub. No.: WO2017/030056
PCT Pub. Date: Feb. 23, 2017

(65) Prior Publication Data
US 2018/0232886 A1    Aug. 16, 2018

(30) Foreign Application Priority Data

Aug. 19, 2015   (JP) ................................ 2015-162124

(51) Int. Cl.
*G06T 7/13*    (2017.01)
*G06T 1/00*    (2006.01)
(Continued)

(52) U.S. Cl.
CPC .................. *G06T 7/13* (2017.01); *A61B 3/10* (2013.01); *A61B 3/102* (2013.01); *G06T 1/00* (2013.01);
(Continued)

(58) Field of Classification Search
CPC .. A61B 3/10; A61B 3/102; G06T 1/00; G06T 7/143; G06T 7/13; G06T 7/0014;
(Continued)

(56) References Cited

U.S. PATENT DOCUMENTS

2005/0140984 A1* 6/2005 Hitzenberger ......... A61B 3/102
356/497
2009/0066723 A1* 3/2009 Saito .................... H04N 9/3147
345/629

(Continued)

FOREIGN PATENT DOCUMENTS

| JP | 2010279438 | 12/2010 |
|---|---|---|
| JP | 2011030911 | 2/2011 |

(Continued)

OTHER PUBLICATIONS

European Search Report dated Jan. 21, 2019 issued in Application No. 16 837 046.8.

(Continued)

*Primary Examiner* — Brenda C Bernardi
(74) *Attorney, Agent, or Firm* — Adams & Wilks

(57) ABSTRACT

Edges of layers are detected from an input image to create a boundary line candidate image that represents the detected edges. A luminance value of the input image is differentiated to create a luminance value-differentiated image that represents luminance gradient of the layers. An evaluation score image is created which is obtained by weighting calculation at an optimum ratio between a boundary line position probability image and the luminance value-differentiated (Continued)

image. The boundary line position probability image is obtained from the boundary line candidate image and an existence probability image that represents existence of a boundary line to be extracted. A route having the highest total evaluation score is extracted as the boundary line. According to such an image processing apparatus and image processing method, boundary lines of layers can be extracted with a high degree of accuracy from a captured image of a target object composed of a plurality of layers.

21 Claims, 15 Drawing Sheets

(51) Int. Cl.
  *A61B 3/10* (2006.01)
  *G06T 7/143* (2017.01)
  *G06T 7/00* (2017.01)
(52) U.S. Cl.
  CPC ............ *G06T 7/0014* (2013.01); *G06T 7/143* (2017.01); *G06T 2207/10101* (2013.01); *G06T 2207/20076* (2013.01); *G06T 2207/30041* (2013.01)
(58) Field of Classification Search
  CPC . G06T 2207/30041; G06T 2207/10101; G06T 2207/20076
  See application file for complete search history.

(56) References Cited

U.S. PATENT DOCUMENTS

| 2011/0141259 | A1 | 6/2011 | Nakano ........................... 348/78 |
| 2011/0182517 | A1 | 7/2011 | Farsiu et al. ................... 382/190 |
| 2012/0070059 | A1 | 3/2012 | Furukawa et al. ............. 382/131 |
| 2012/0328156 | A1 | 12/2012 | Nakano et al. ................. 382/103 |
| 2013/0004046 | A1 | 1/2013 | Nakano et al. ................. 382/131 |
| 2014/0063447 | A1 | 3/2014 | Piotrowski et al. ........... 351/206 |
| 2014/0334703 | A1* | 11/2014 | Farsiu .................. A61B 5/0066 382/131 |

FOREIGN PATENT DOCUMENTS

| JP | 2011194060 | 10/2011 |
| JP | 2011194061 | 10/2011 |
| JP | 2012061337 | 3/2012 |
| JP | 2014045905 | 3/2014 |
| JP | 5665768 | 2/2015 |

OTHER PUBLICATIONS

Andrew Lang et al: "Retinal layer segmentation of macular OCT images using boundary classification", Biomedical Optics Express, vol. 4, No. 7, Jun. 14, 2013.
Yang, Q. "Automated layer segmentation of macular OCT images using dual-scale gradient information", Optics Express, vol. 18, No. 20 (Sep. 27, 2010), pp. 21293-21307.
International Search Report dated Oct. 18, 2016 in International Application No. PCT/JP2016/073496 together with English-language translation thereof.

\* cited by examiner

[FIG. 1]
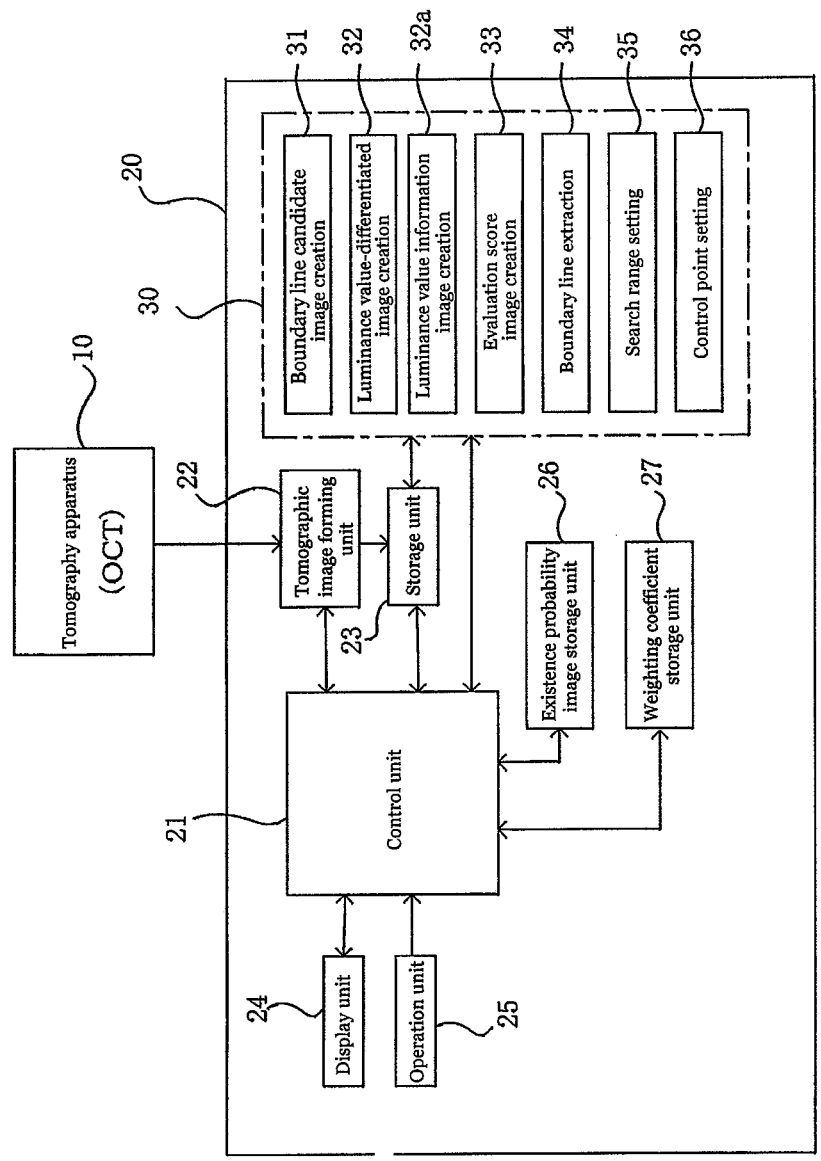

[FIG. 2]
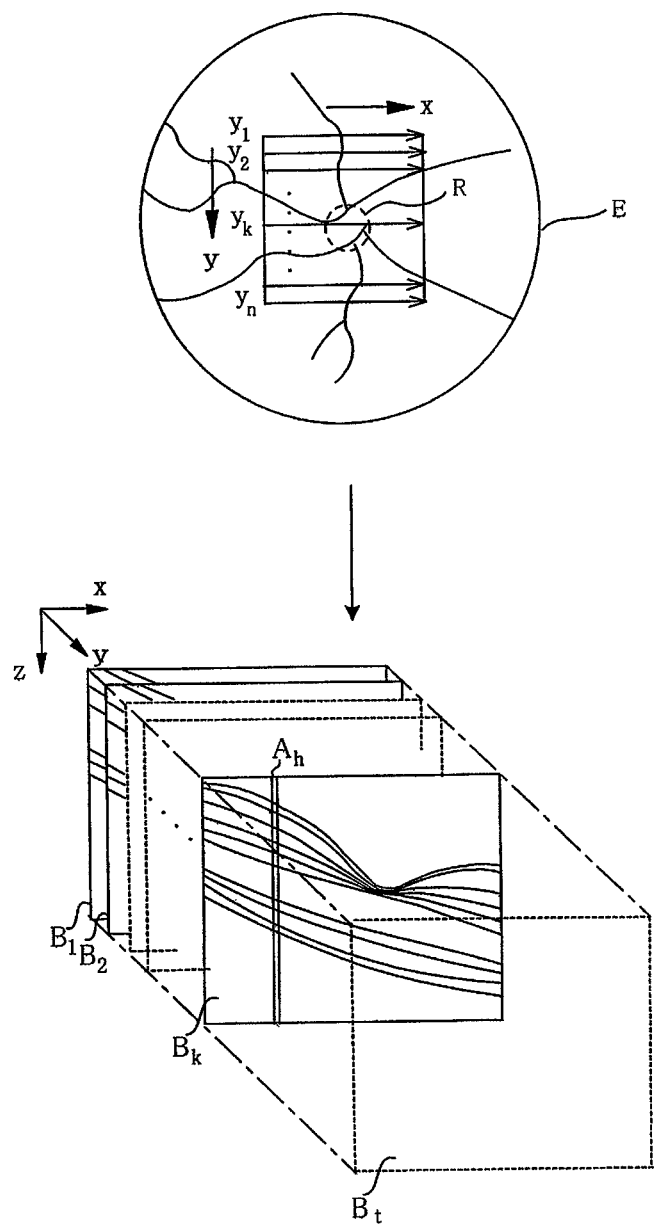

[FIG. 3]
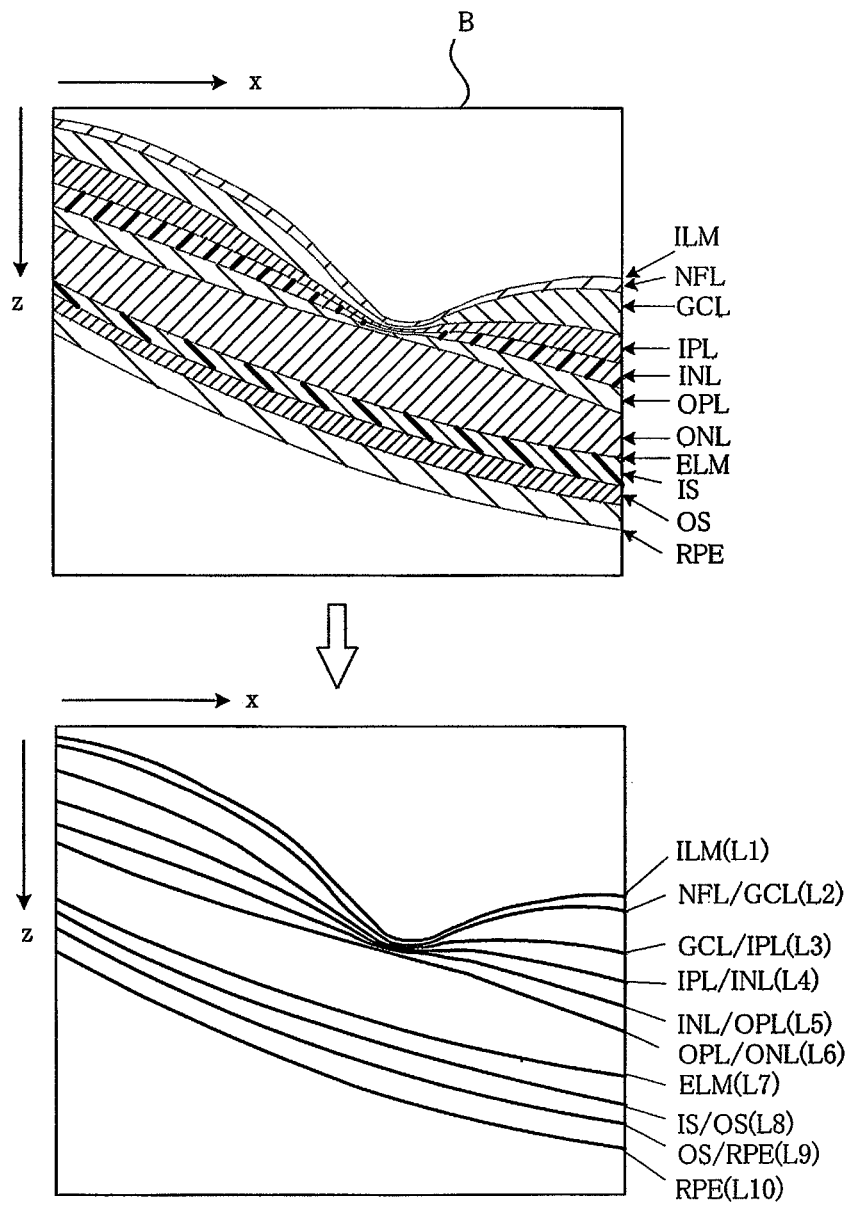

[FIG. 4]
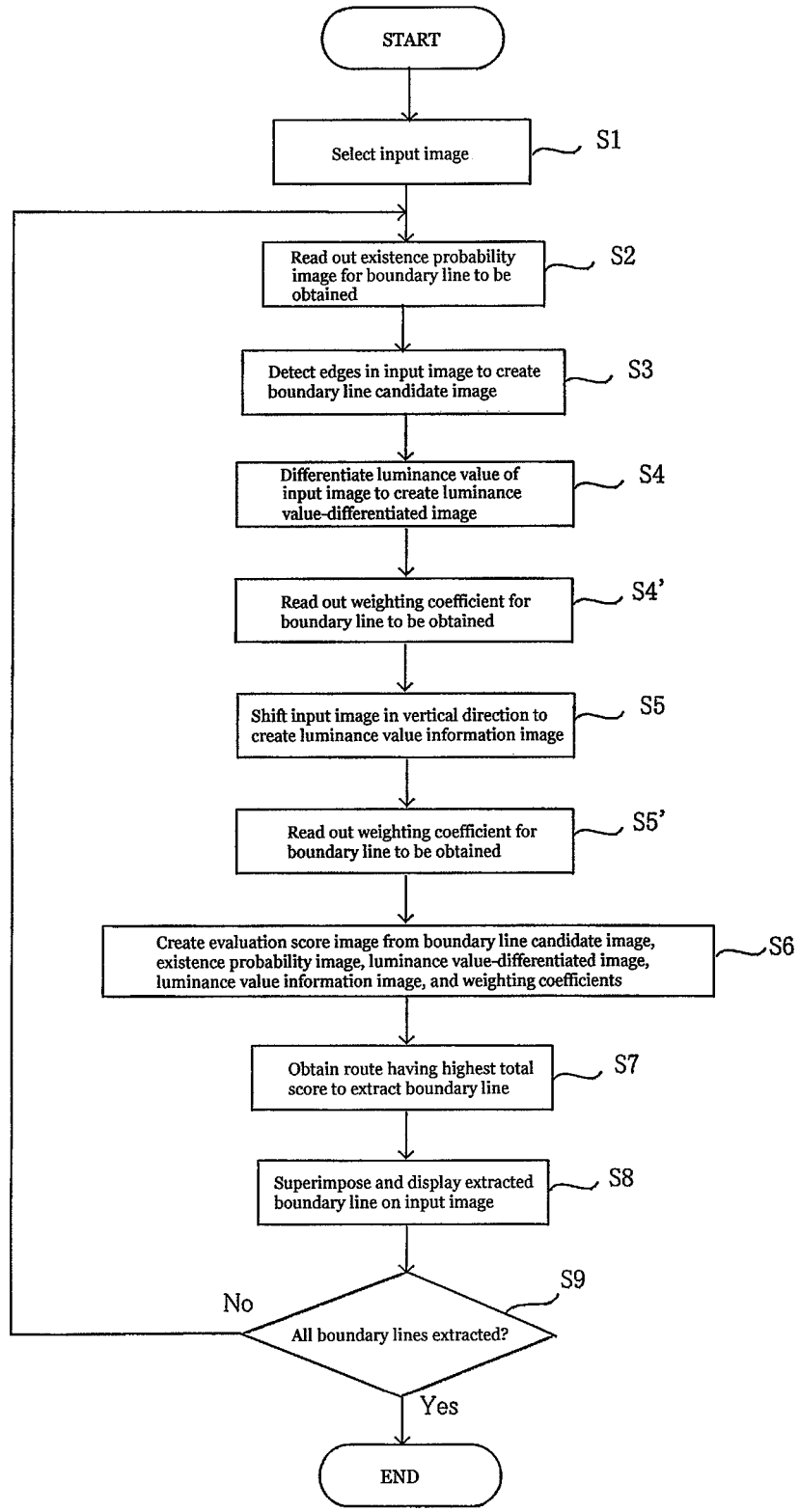

[FIG. 5]
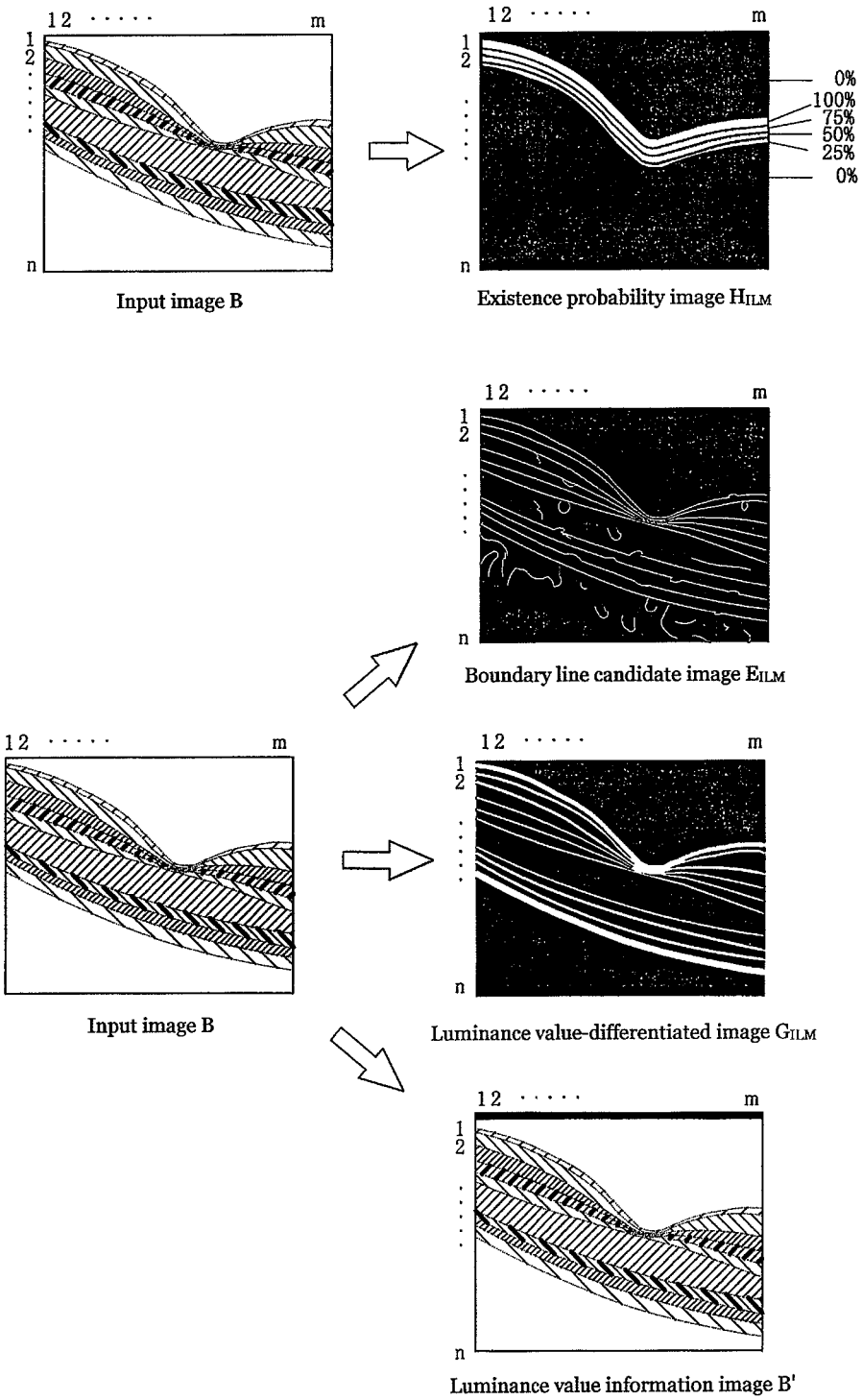

[FIG. 6]
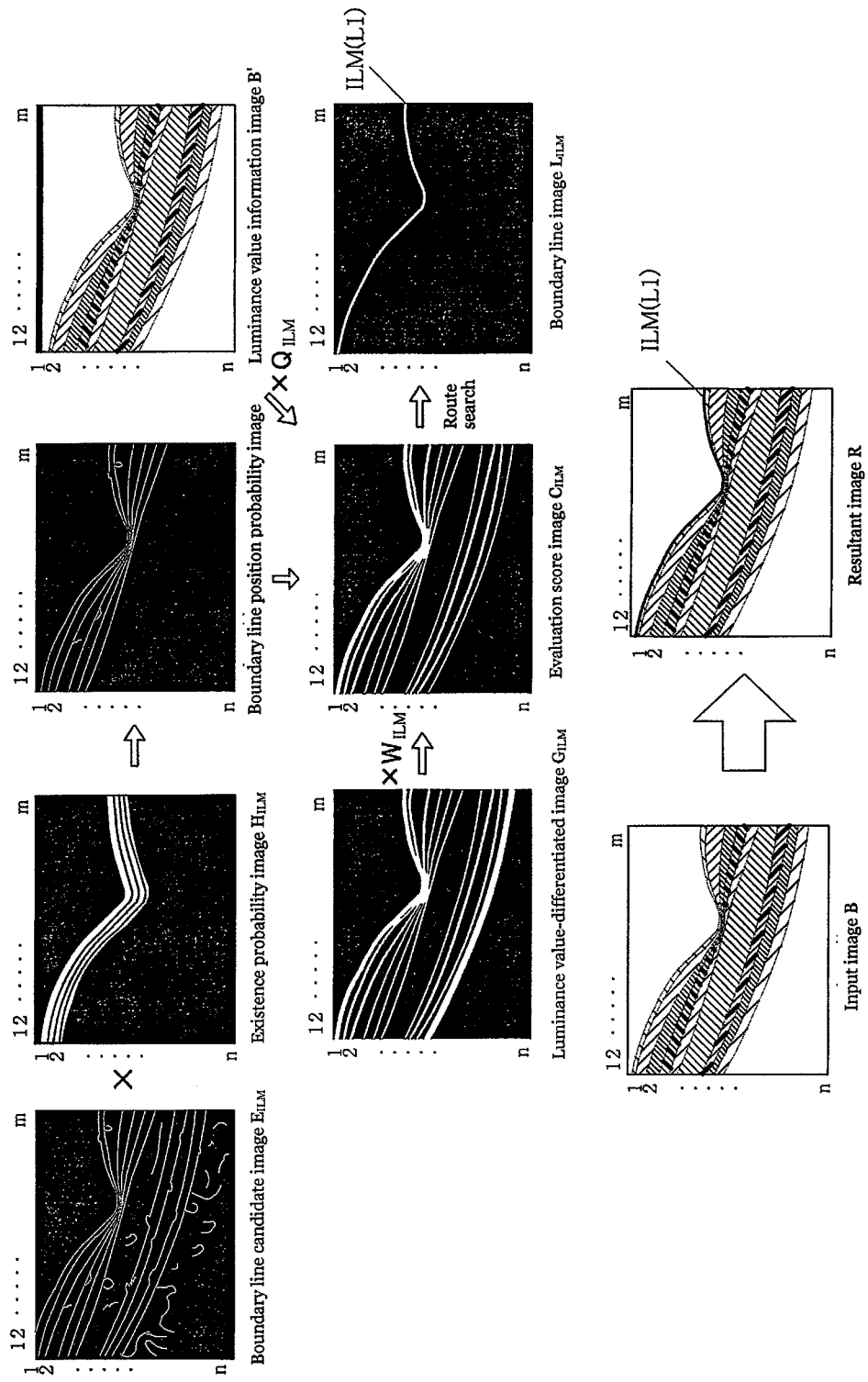

[FIG. 7]
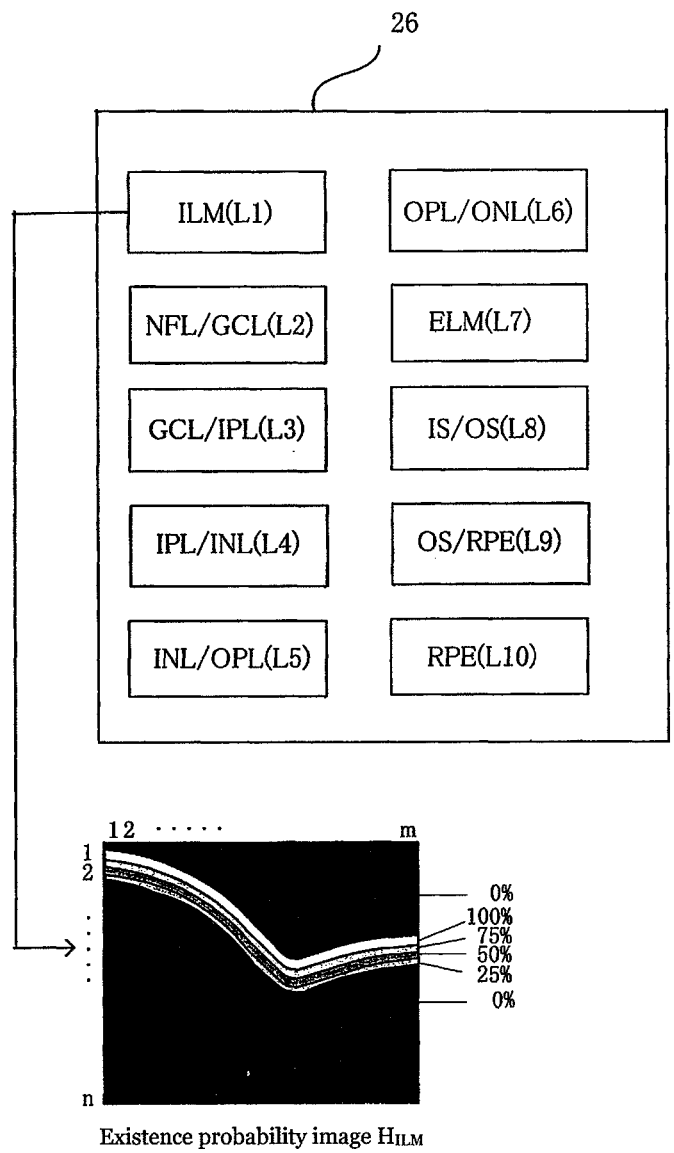
Existence probability image $H_{ILM}$

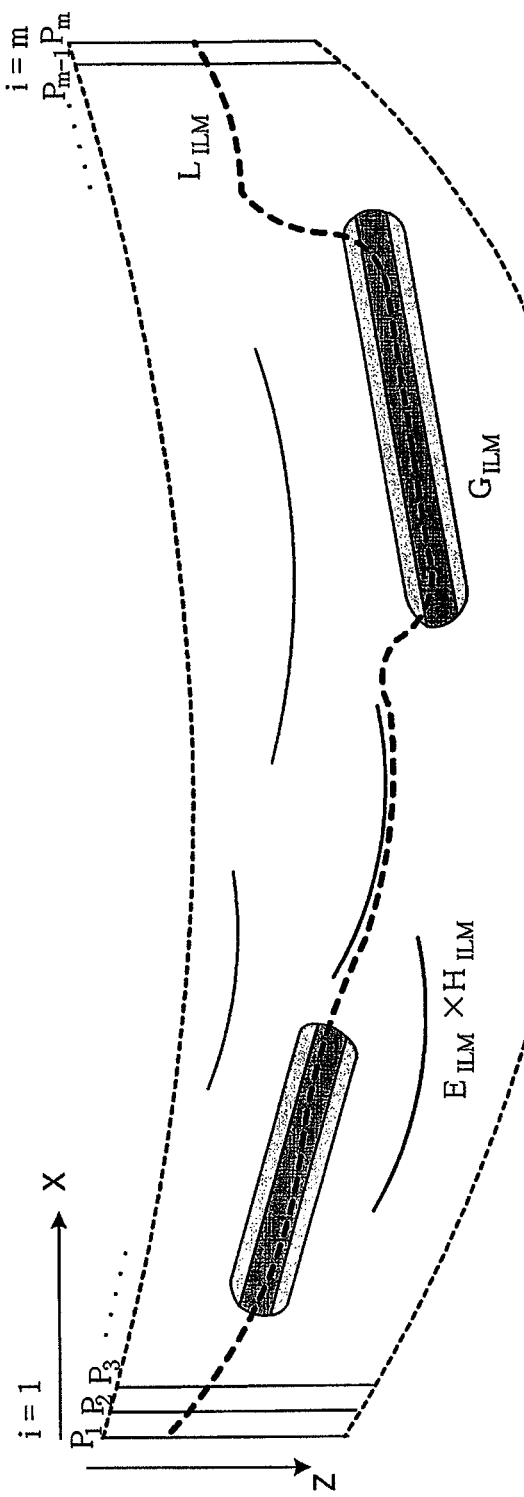
[FIG. 8]

[FIG. 9]
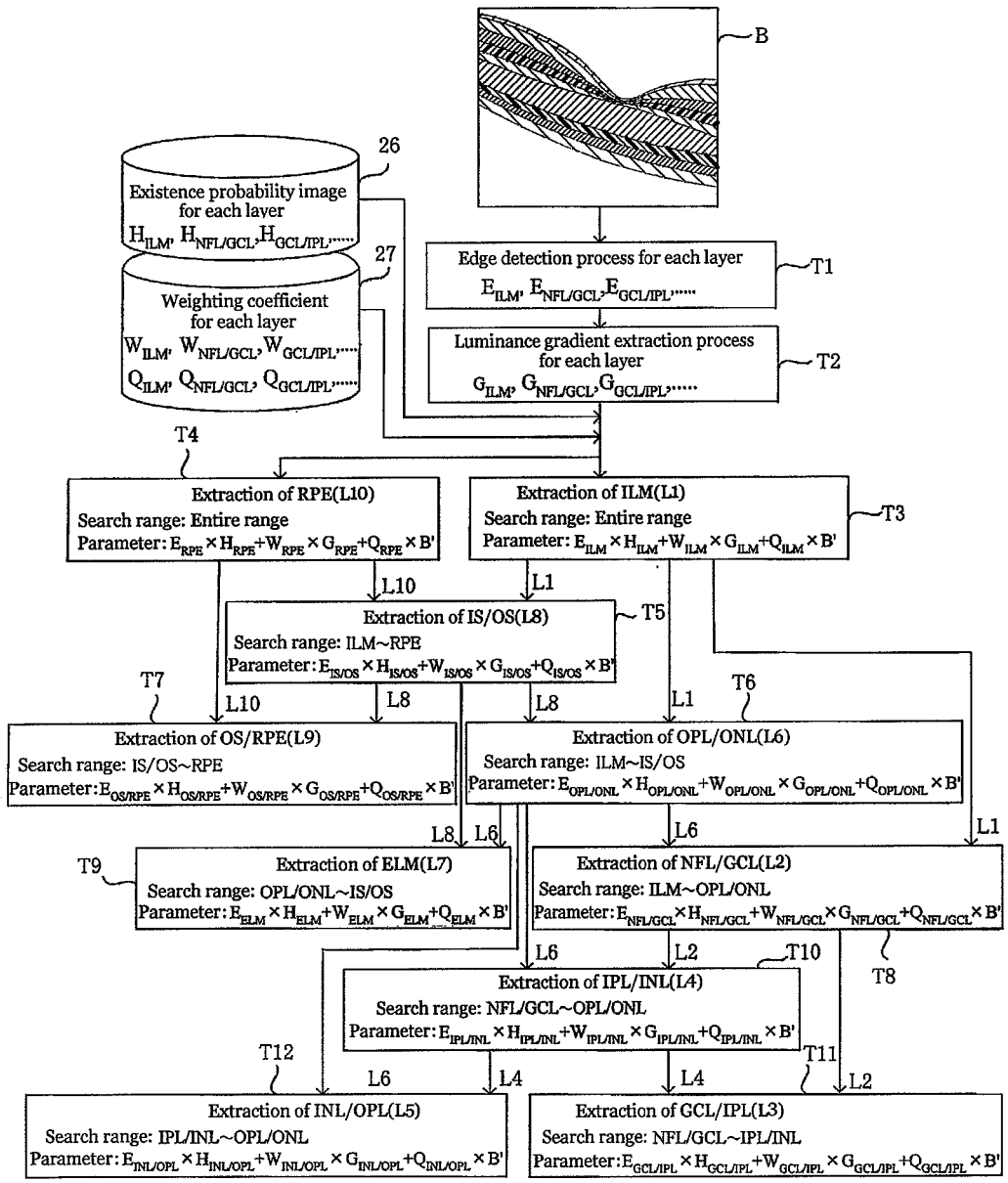

[FIG. 10]
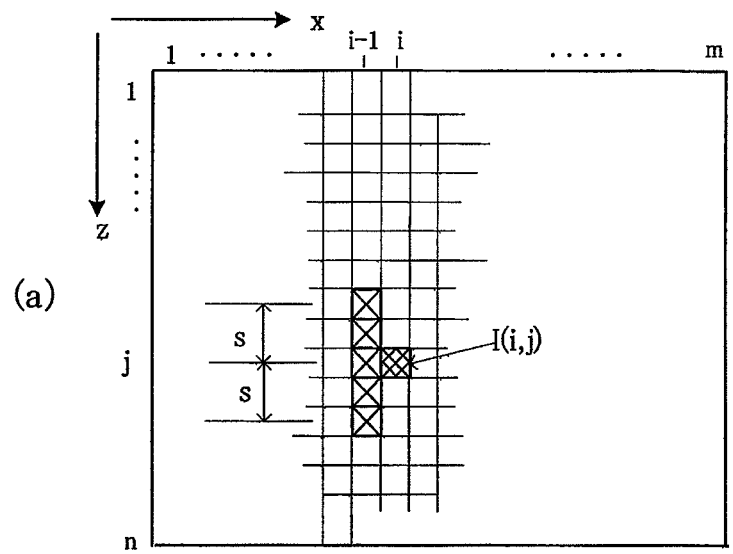
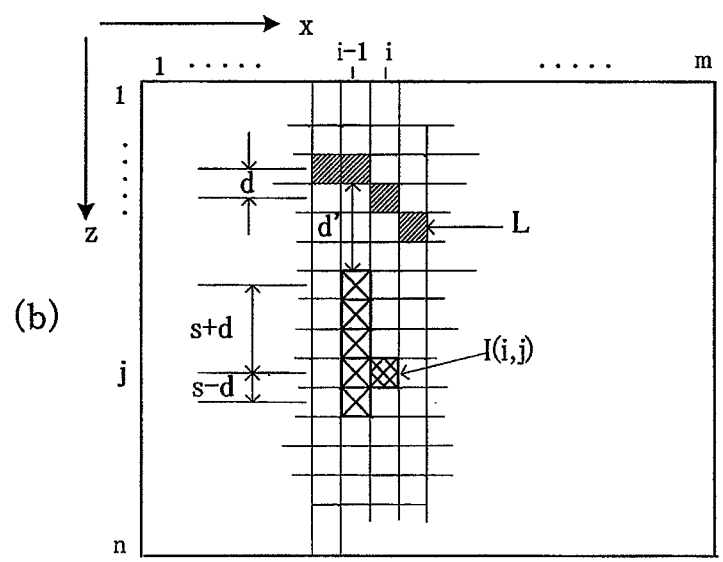

[FIG. 11]
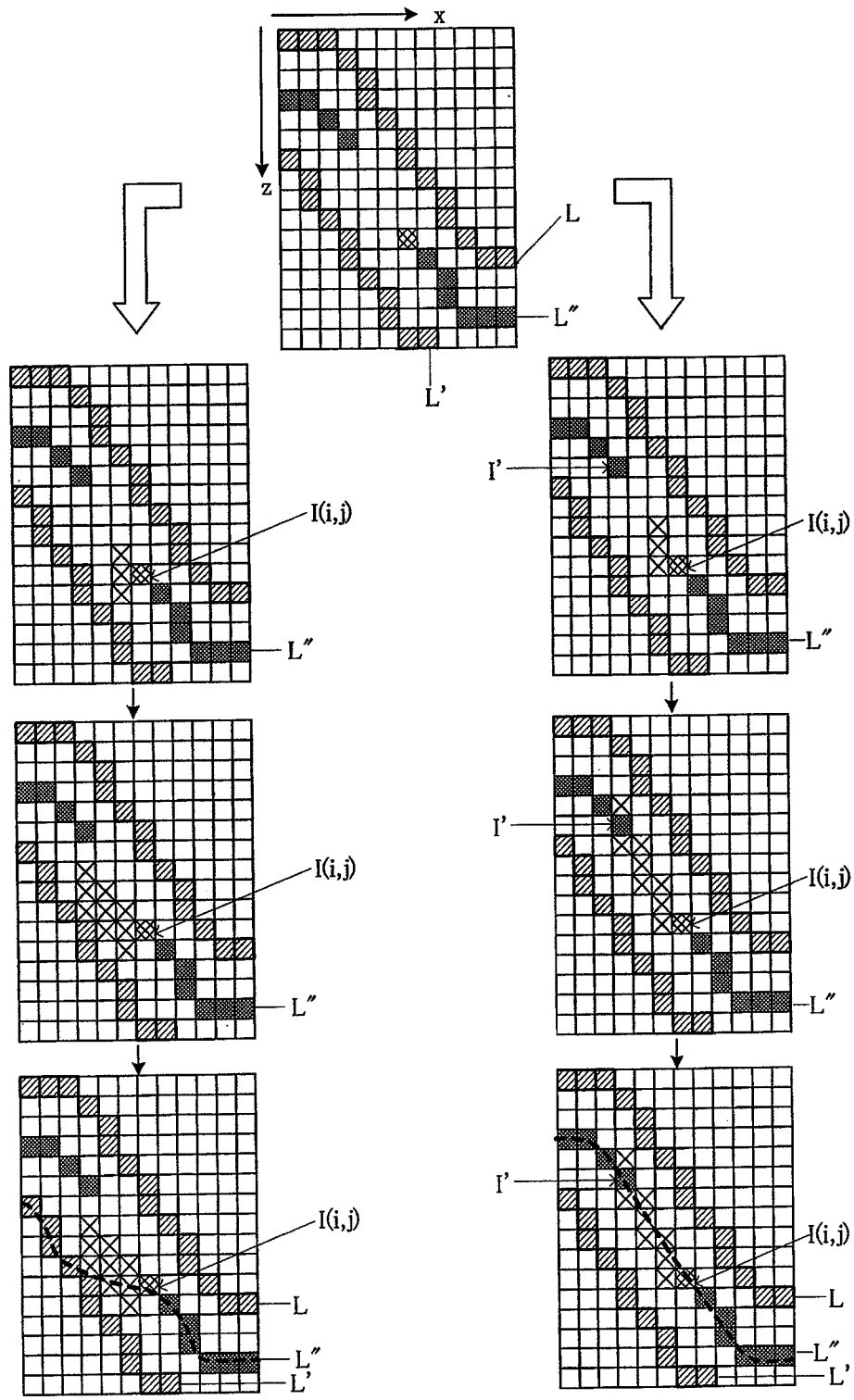

[FIG. 12]
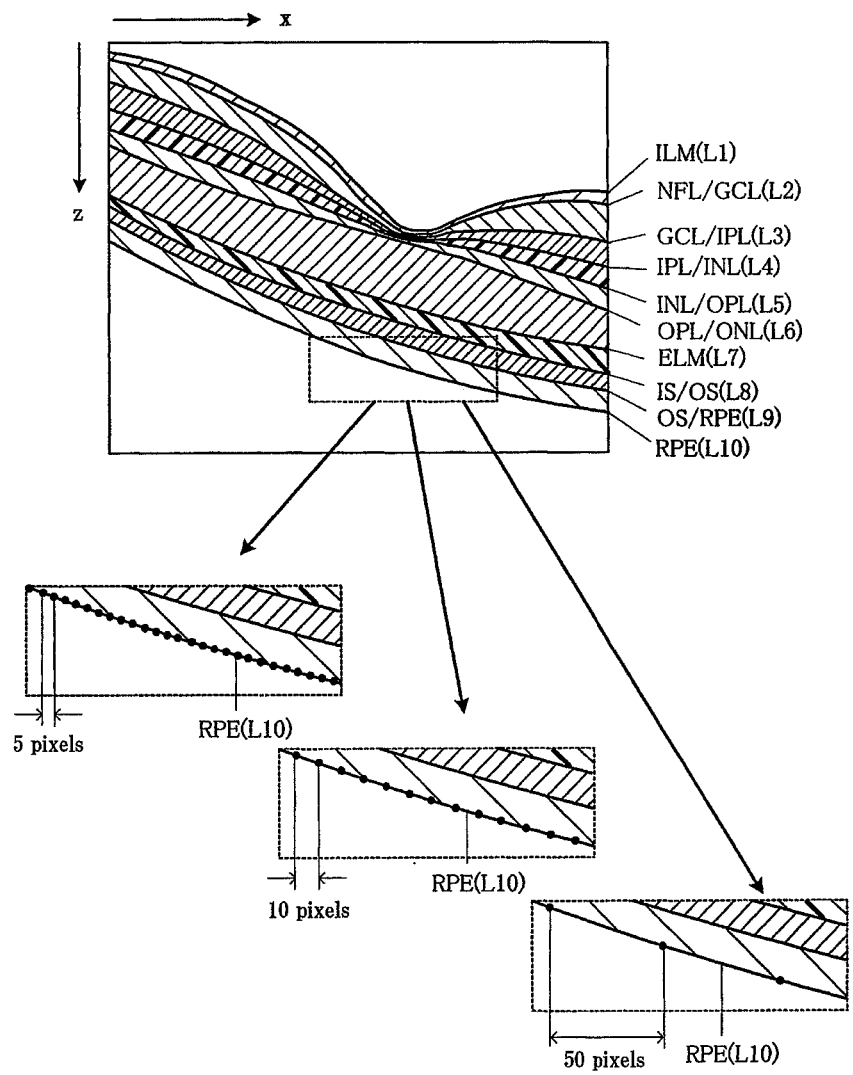

[FIG. 13]
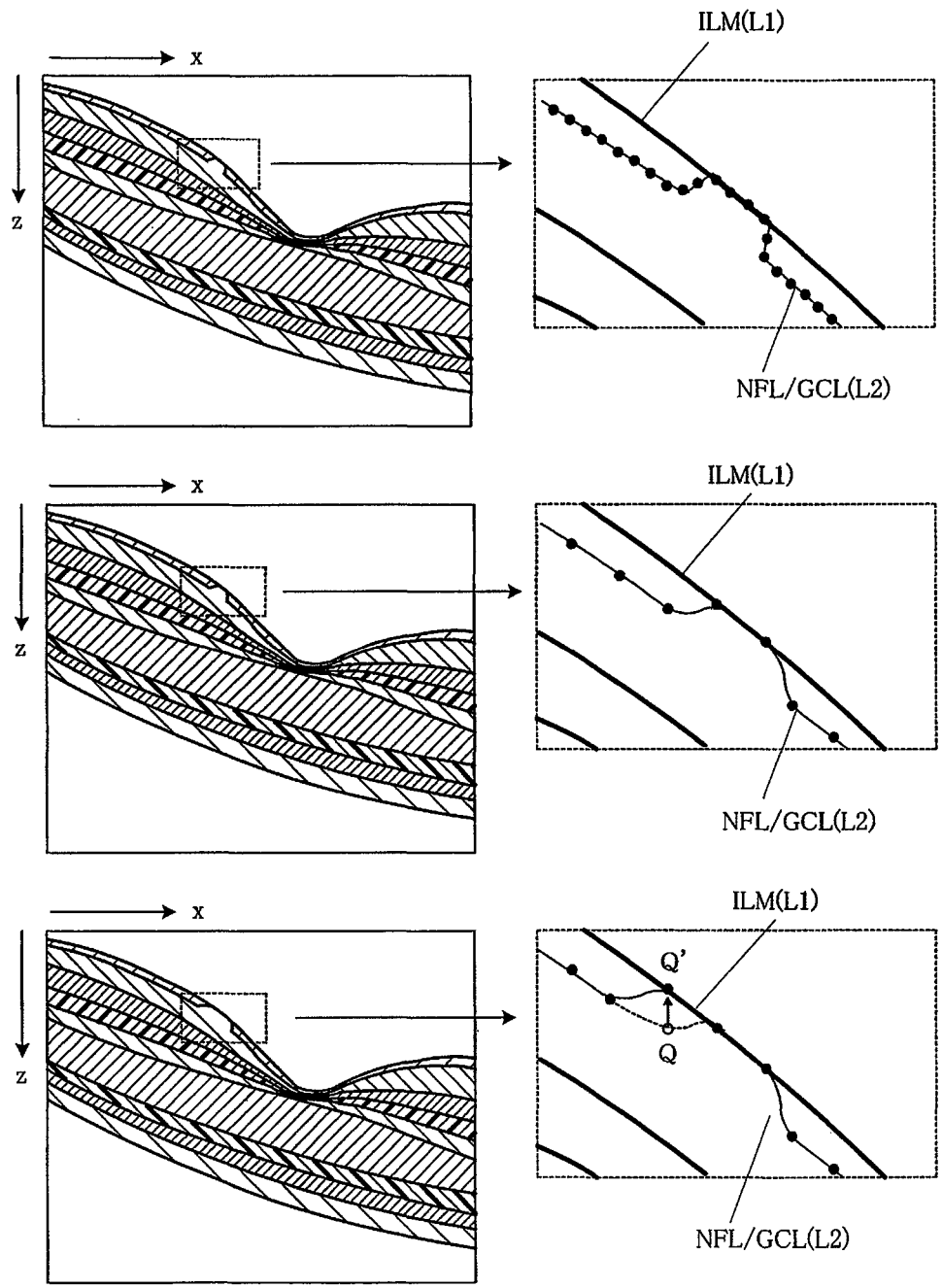

[FIG. 14]
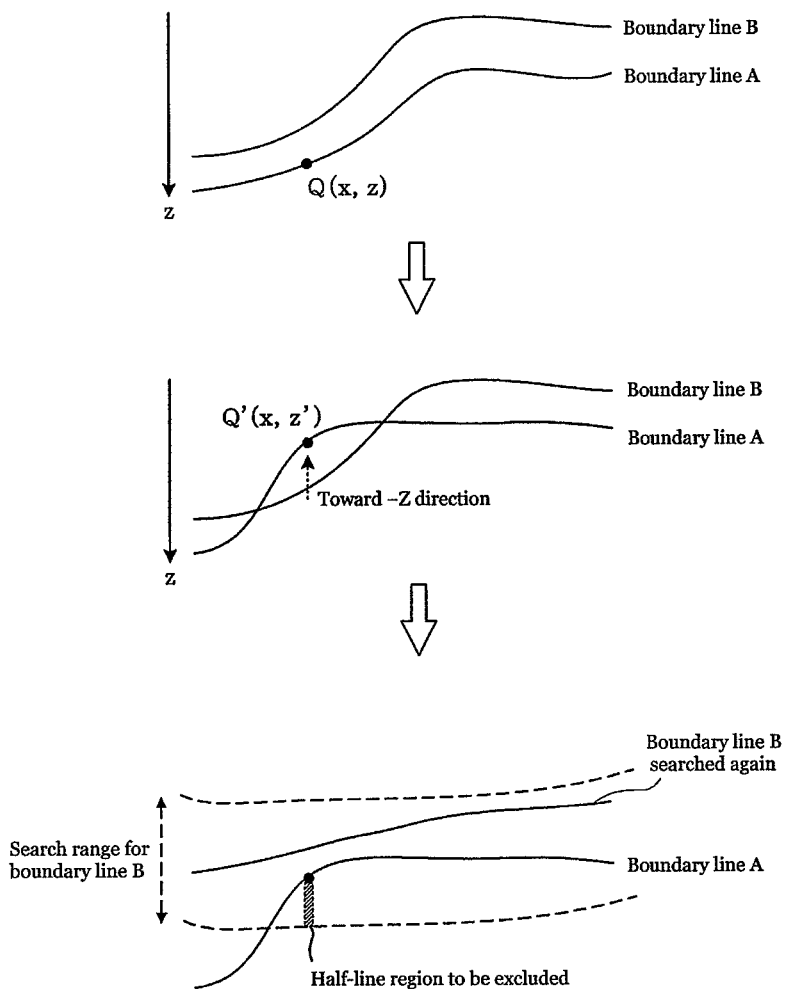

[FIG. 15]
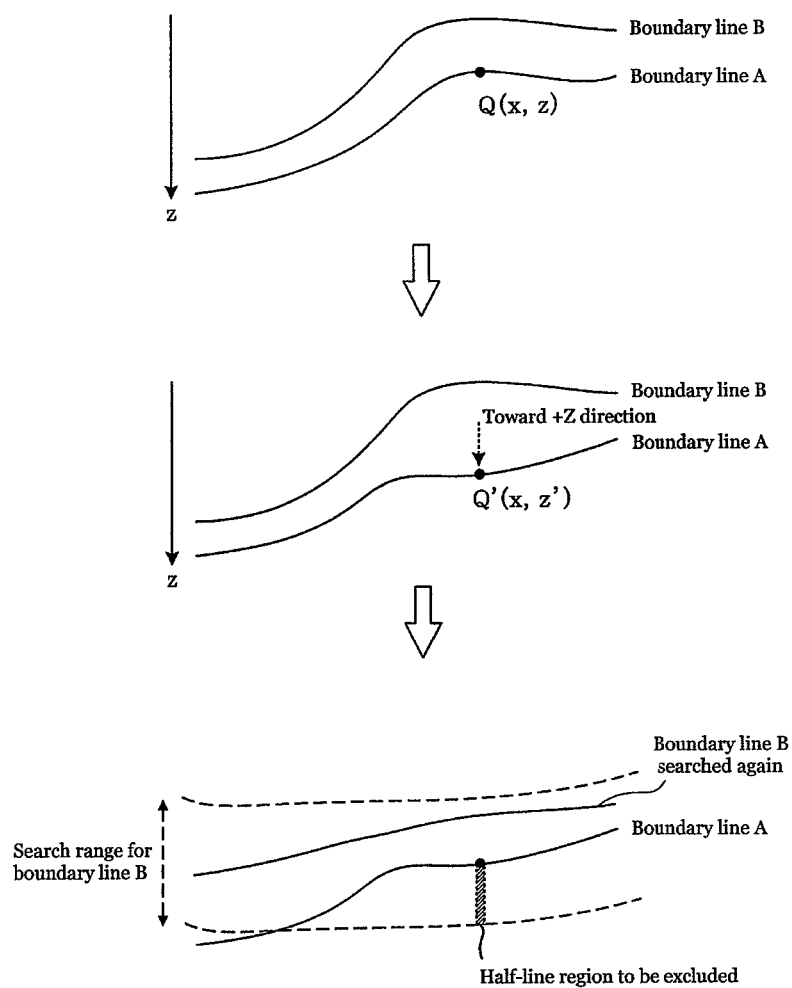

IMAGE PROCESSING APPARATUS, IMAGE PROCESSING METHOD, AND IMAGE PROCESSING PROGRAM

TECHNICAL FIELD

The present invention relates to an image processing apparatus, an image processing method, and an image processing program for extracting boundary lines of layers by processing a tomographic image of a target object, such as a tomographic image of a subject's eye, captured using a tomography apparatus or the like.

BACKGROUND ART

One of ophthalmic diagnostic apparatuses is a tomography apparatus that utilizes optical interference of so-called optical coherence tomography (OCT) to capture tomographic pictures of ocular fundi. Such a tomography apparatus can irradiate an ocular fundus with low-coherence light of broadband as the measurement light to capture tomographic pictures of the ocular fundus with high sensitivity through interference of the reflected light from the ocular fundus and reference light.

Such a tomography apparatus is capable of three-dimensionally observing the state inside the retinal layers. For example, it is possible to quantitatively diagnose the stage of progression of ophthalmic disorder, such as glaucoma, and the degree of recovery after the treatment through measurement of the layer thickness of a retinal layer, such as a nerve fiber layer, or the change in a layer shape, such as irregularities, on a retinal pigment epithelium layer.

Patent Literature 1 describes a configuration for detecting the boundary of a retinal layer from a tomographic picture captured by a tomography apparatus and extracting exudates as one of lesions from the ocular fundus image.

Patent Literature 2 describes a configuration for identifying an artifact region in the tomographic image of an ocular fundus, detecting the boundary of a retinal layer in a region that is not an artifact region, detecting the boundary of a retinal layer in the artificial region on the basis of luminance values in a different method, and superimposing and displaying lines that represent the detected boundaries.

Patent Literature 3 describes a configuration for detecting layers on the basis of edges lying from a side at which the intensity of signal light obtained from a tomographic image of a subject's eye is low to a side at which the intensity of signal light is high and detecting a layer or layer boundary existing between the layers on the basis of an edge lying from the side at which the intensity of signal light is high to a side at which the intensity of signal light is low.

Patent Literature 4 describes a configuration for preliminarily setting an existence probability model in which the existence probability of brain tissues in the three-dimensional space of an MRI image is modeled, obtaining a tissue distribution model in which both the signal intensity distribution model and the existence probability model are established, and calculating, for each voxel included in the MRI image, a degree of the voxel belonging to white matter tissues and gray white tissues.

Non-Patent Literature 1 describes a configuration for acquiring an edge image of a retinal tomographic picture using a Canny edge detection method, weighting the edge image and a luminance gradient image to calculate them, and searching a shortest route to extract a boundary line of the retinal layer. Non-Patent Literature 1 also describes a configuration for first extracting two boundary lines when extracting boundary lines of a plurality of retinal layers, and searching another boundary line existing therebetween within a narrow range interposed between the extracted boundary lines, thereby reducing the extraction time.

PRIOR ART LITERATURE

Patent Literature

[Patent Literature 1] JP2010-279438A
[Patent Literature 2] JP2012-61337A
[Patent Literature 3] JP5665768B
[Patent Literature 4] JP2011-30911A

Non-Patent Literature

[Non-Patent Literature 1] "Automated layer segmentation of macular OCT images using dual-scale gradient information" 27 Sep. 2010/Vol. 18, No, 20/OPTICS EXPRESS 21293-21307

SUMMARY OF THE INVENTION

Problems to be Solved by the Invention

In the configuration of Patent Literature 1 to 3, however, the boundary line of a layer is extracted by detecting an edge in the tomographic image and, therefore, the accuracy in extracting the boundary line depends on the edge detection. Problems thus exist in that the edge information cannot be obtained with a sufficient degree of accuracy in a region in which the luminance value is low and it is difficult to perform reliable boundary line extraction.

In the configuration of Patent Literature 2, the position of a layer is obtained in the artifact region, in which the luminance value is low, using an evaluation function value for a model shape. However, the accuracy of the evaluation function value is insufficient and a problem exists in that the accuracy in extracting the boundary line deteriorates in a region in which the luminance value is low.

In Non-Patent Literature 1, the edge image of a retinal tomographic picture and the luminance gradient image are each weighted to extract the boundary line. However, the weighting is one-dimensional and, in particular, the edge image is not associated with the probability of existence of the boundary line to be extracted. A disadvantage is therefore that the boundary line cannot be extracted with a high degree of accuracy.

In Patent Literature 4, the existence probability model representing the existence probability of brain tissues is used to calculate a degree that a region of the brain tissues belongs to white matter tissues and gray white tissues, but a problem exists in that the calculation takes time because the existence probability model is a three-dimensional model.

In Non-Patent Literature 1, the extraction time is reduced through extracting two boundary lines and searching another boundary line existing therebetween within a narrow range interposed between the extracted boundary lines. However, Non-Patent Literature 1 involves a problem in that the extracted boundary line may cross another boundary line that has already been extracted or an ambiguous boundary line or disappearing boundary line can not be extracted with a high degree of accuracy because a process of restricting the extraction region on the basis of extracted results and further restricting the extraction region on the basis of extracted results is not repeated and sequentially performed.

The present invention has been made in consideration of the above and objects of the present invention include providing an image processing apparatus, an image processing method, and an image processing program that are able to extract boundary lines of layers with a high degree of accuracy from a captured image of a target object that is composed of a plurality of layers.

Means for Solving the Problems

The present invention is characterized by
creating a boundary line candidate image using an input image obtained by capturing an image of a target object composed of a plurality of layers, the boundary line candidate image representing edges of the layers detected from the input image as boundary line candidates,
differentiating a luminance value of the input image to create a luminance value-differentiated image, the luminance value-differentiated image representing luminance gradient of the layers, and
performing a route search to extract a boundary line, the route search being performed on the basis of a boundary line position probability image and the luminance value-differentiated image, the boundary line position probability image representing a boundary line position and created from the boundary line candidate image and an existence probability image, the existence probability image representing existence of the boundary line to be extracted.

The luminance value-differentiated image may be weighted with a weighting coefficient in accordance with the boundary line to be extracted.

The existence probability image may be read out from an existence probability image storage unit in accordance with the boundary line to be extracted. The existence probability image storage unit may store the existence probability image for each boundary line of the layers. The weighting coefficient may be read out from a weighting coefficient storage unit in accordance with the boundary line to be extracted. The weighting coefficient storage unit may store the weighting coefficient for each boundary line of the layers.

An evaluation score image may be created on the basis of the boundary line position probability image and the luminance value-differentiated image. The boundary line position probability image may be created from the boundary line candidate image and the existence probability image which represents existence of the boundary line to be extracted. A boundary line extracting means may be provided to search for a route having a highest total evaluation score from the created evaluation score image and extract the route having the highest total evaluation score as the boundary line.

When the extracted boundary line is modified, the existence probability image for the boundary line stored in the storage unit may be modified. When the weighting coefficient is modified, the weighting coefficient for the boundary line stored in the storage unit may be modified.

Advantageous Effect of the Invention

According to an aspect of the present invention, the boundary line may be extracted through obtaining boundary position information of the input image using the existence probability image, obtaining luminance value information of the information using the luminance value-differentiated image, and combining the boundary position information and the luminance value information. The boundary line can therefore be extracted with a high degree of accuracy.

Moreover, according to an aspect of the present invention, in a portion in which the boundary line to be extracted exists, the evaluation score is high due to calculation using the existence probability image. The accuracy in extracting the boundary line can therefore be remarkably improved.

Furthermore, the luminance information may be weighted in accordance with the boundary line to be extracted, thereby to allow highly-accurate extraction of boundary lines having different characteristics.

BRIEF DESCRIPTION OF DRAWINGS

FIG. 1 is a block diagram illustrating the overall configuration of an image processing apparatus.

FIG. 2 is an explanatory view illustrating a state of acquiring a tomographic image of an ocular fundus retina by scanning the ocular fundus.

FIG. 3 is an explanatory view illustrating retinal layers and their boundary lines in the acquired tomographic image.

FIG. 4 is a flowchart illustrating steps of extracting boundary lines of retinal layers.

FIG. 5 is an explanatory view illustrating an existence probability image that is read out on the basis of an input image and a boundary line candidate image and a luminance value-differentiated image that are created from the input image.

FIG. 6 is an explanatory view illustrating a process of extracting a boundary line from the input image to acquire a resultant image.

FIG. 7 is a block diagram illustrating the configuration of an existence probability image storage unit.

FIG. 8 is an explanatory view illustrating a route search for extracting a boundary line.

FIG. 9 is a flowchart illustrating a process of extracting a plurality of boundary lines.

FIG. 10(a) is an explanatory view illustrating a method of fixedly setting a search range to extract a boundary line and FIG. 10(b) is an explanatory view illustrating a method of dynamically setting a search range to extract a boundary line.

FIG. 11 is an explanatory view illustrating a method of extracting an ambiguous or disappearing boundary line.

FIG. 12 is an explanatory view illustrating a state in which control points are displayed on an extracted boundary line at changed pixel intervals.

FIG. 13 is an explanatory view illustrating a state in which control points are displayed on an extracted boundary line at changed pixel intervals and a control point is moved to modify the boundary line.

FIG. 14 is an explanatory view (part 1) illustrating a method of performing a route search again after moving a control point, to extract another boundary line.

FIG. 15 is an explanatory view (part 2) illustrating a method of performing a route search again after moving a control point, to extract another boundary line.

EMBODIMENTS FOR CARRYING OUT THE INVENTION

Hereinafter, the present invention will be described in detail on the basis of one or more examples or embodiments with reference to the drawings. Description will be made herein by exemplifying tomographic images of the ocular fundus of a subject's eye as images of a target object to be processed, but images of a target object to be processed in the present invention are not limited to tomographic images of an ocular fundus and the present invention can be applied to images of a target object for which images of a plurality of layers are captured.

EXAMPLE 1

<Overall Configuration>

FIG. 1 is a block diagram illustrating the entire system which acquires tomographic images of the ocular fundus of a subject's eye and processes the images. This system includes a tomography apparatus 10. The tomography apparatus 10 is an apparatus that captures tomographic pictures of the ocular fundus of a subject's eye using optical coherence tomography (OCT) and operates, for example, in a Fourier-domain scheme. Since the tomography apparatus 10 is well known in the art, its detailed explanation will be omitted. The tomography apparatus 10 is provided with a low-coherence light source, the light from which is split into reference light and signal light. As illustrated in FIG. 2, the signal light is raster-scanned on an ocular fundus E, for example, in the X and Y directions. The signal light scanned and reflected from the ocular fundus E is superimposed with the reference light reflected from a reference mirror to generate interference light. On the basis of the interference light, OCT signals are generated which represent information in the depth direction (Z direction) of the ocular fundus.

The system further includes an image processing apparatus 20. The image processing apparatus 20 has a control unit 21 that is realized by a computer composed of a CPU, a RAM, a ROM, and other necessary components. The control unit 21 executes an image processing program thereby to control the entire image processing. The image processing apparatus 20 is provided with a tomographic image forming unit 22.

The tomographic image forming unit 22 is realized by a dedicated electronic circuit that executes a known analyzing method, such as a Fourier-domain scheme, or by an image processing program that is executed by the previously-described CPU. The tomographic image forming unit 22 forms tomographic images of an ocular fundus on the basis of the OCT signals generated from the tomography apparatus 10.

For example, as illustrated in FIG. 2, when the ocular fundus E is scanned in the X direction at positions of $y_N$ (N=1, 2, . . . , n) along the Y direction, sampling is performed multiple times (m times) for each scan. Tomographic images (A-scan images) $A_h$ (h=1, 2, . . . , m) in the Z direction are acquired at respective sampling points in the X direction, and tomographic images $B_N$ (N=1, 2, . . . , t) are formed from the A-scan images $A_h$. Each A-scan image is stored, for example, with a width of one pixel in the X direction and a length of n pixels in the Z direction and, therefore, each tomographic image $B_N$ is an image having a size of m×n pixels, which is also referred to as a B-scan image.

A plurality (t) of tomographic images $B_N$ formed by the tomographic image forming unit 22 or a three-dimensional volume image assembled from the t tomographic images $B_N$ is stored in a storage unit 23 composed of a semiconductor memory, hard disk drive, or other appropriate storage device. The storage unit 23 further stores the above-described image processing program and other necessary programs and data.

The image processing device 20 is provided with an image processing unit 30. The image processing unit 30 comprises a boundary line candidate image creating means 31, a luminance value-differentiated image creating means 32, a luminance value information image creating means 32a, an evaluation score image creating means 33, a boundary line extracting means 34, a search range setting means 35, and a control point setting means 36.

As will be described later, the boundary line candidate image creating means 31 detects edges in an input image to create a boundary line candidate image, the luminance value-differentiated image creating means 32 differentiates the luminance value of the input image to create a luminance value-differentiated image that represents a luminance gradient, the luminance value information image creating means 32a shifts the input image in the vertical direction to create a luminance value information image that represents luminance information, the evaluation score image creating means 33 creates an evaluation score image that represents an evaluation score for boundary line extraction, on the basis of the created images and read-out images, and the boundary line extracting means 34 searches for a route having the highest total value of the evaluation score from the evaluation score image and extracts it as a boundary line. The search range setting means 35 sets a search range to match one or more already extracted boundary lines, and the control point setting means 36 sets control points at a certain pixel interval on the extracted boundary line. Each means or each image processing in the image processing unit 30 is realized by using a dedicated electronic circuit or by executing the image processing program.

An existence probability image storage unit 26 is provided to store, for each boundary line to be extracted, an image that represents the existence probability of the boundary line, as will be described later.

A weighting coefficient storage unit 27 is provided to store a weighting coefficient with which the luminance value-differentiated image is weighted and a weighting coefficient with which the luminance value information image is weighted, for each boundary line to be extracted.

A display unit 24 is provided which is, for example, composed of a display device such as an LCD. The display unit 24 displays tomographic images stored in the storage unit 23, images generated or processed by the image processing apparatus 20, control points set by the control point setting means 36, associated information such as information regarding the subject, and other information.

An operation unit 25 is provided which, for example, has a mouse, keyboard, operation pen, pointer, operation panel, and other appropriate components. The operation unit 25 is used for selection of an image displayed on the display unit 24 or used for an operator to give an instruction to the image processing apparatus 20 or the like.

Among the tomographic images captured using such a configuration, the tomographic image $B_k$ acquired with the scanning line $y_k$ passing through a macula region R of the ocular fundus E illustrated in FIG. 2 is presented in the upper part of FIG. 3 with reference character B. The retina of an ocular fundus is composed of tissues of various membranes or layers. FIG. 3 illustrates the membranes or layers which can be distinguished in the tomographic image B.

Specifically, FIG. 3 illustrates an internal limiting membrane ILM, a nerve fiber layer NFL, a ganglion cell layer GCL, an inner plexiform layer IPL, an inner nuclear layer INL, an outer plexiform layer OPL, an outer nuclear layer ONL, an external limiting membrane ELM, inner photoreceptor segments IS, outer photoreceptor segments OS, and a retinal pigment epithelium RPE.

In the lower part of FIG. 3, boundary lines of or between these membranes or layers are illustrated with parenthesized L1 to L10. For example, L1 represents a boundary line formed by the internal limiting membrane ILM and L2 represents a boundary line between the nerve fiber layer NFL and the ganglion cell layer GCL. These boundary lines L1 to L10 are boundary lines that are expected to be extracted in the present invention.

If such a tomographic image can be used as the basis to measure the layer thicknesses of the nerve fiber layer and other layers and the change in a layer shape, such as irregularities, on the retinal pigment epithelium layer, it will be possible to quantitatively diagnose the stage of progression of ophthalmic disorder and the degree of recovery after the treatment. Depending on the environment of image capturing, however, accurate measurement of the layer thickness or layer shape may be difficult due to attenuation or missing of OCT signals which causes the boundary line of each layer to be ambiguous or discontinuous or to disappear.

In the present invention, therefore, the following method is employed to extract boundary lines of retinal layers with a high degree of accuracy. This method will be described below with reference to the flowchart of FIG. 4.

<Boundary Line Extracting Process>

First, as illustrated in step S1 of FIG. 4, tomographic images $B_N$ (N=1, 2, . . . , t) from which boundary lines of retinal layers are to be extracted are read out from the storage unit 23 and displayed on the display unit 24, and one or more input images B are selected. The one or more input images may be one of, some of, or all of the t tomographic images $B_N$ illustrated in FIG. 2 or may also be an image to which any image processing is performed. When boundary lines of a plurality of tomographic images are extracted, any one of the tomographic images is selected as an input image. Here, for example, the tomographic image $B_k$ acquired with the scanning line $y_k$ for scanning the macular region R of the ocular fundus of FIG. 2 is read out from the storage unit 23 and employed as an input image B.

After the input image B is selected, a boundary line to be extracted from the input image B is determined and an existence probability image for the boundary line is read out from the existence probability image storage unit 26 (step S2).

The existence probability image storage unit 26 is illustrated in FIG. 7. For the tomographic image $B_k$, the existence probability image storage unit 26 stores an image that represents the existence probability of each of the boundary lines L1 to L10 of the layers in the tomographic image $B_k$. For example, the upper-left ILM(L1) is an image that represents the existence probability of the boundary line L1 of the internal limiting membrane (ILM), and the NFL/GCL (L2) illustrated just below the ILM(L1) is an image that represents the existence probability of the next boundary line L2 between the nerve fiber layer (NFL) and the ganglion cell layer (GCL). Similarly, other existence probability images are stored in the same manner.

Each of such existence probability images is an image comprising m×n pixels that is obtained through preliminarily acquiring the tomographic image $B_K$ with the same scanning line $y_K$ for a plurality of normal eyes, calculating the probability of existence of a boundary line in each pixel (i, j) [i=1, 2, . . . , m, j=1, 2, . . . , n] of the tomographic image $B_K$, and storing the probability of existence as a digital value at a pixel position corresponding to each pixel (i, j) of the tomographic image $B_K$.

For example, the existence probability image ILM(L1) for the boundary line L1 of the tomographic image $B_k$ is schematically illustrated as $H_{ILM}$ in the lower part of FIG. 7, and probability regions (pixel regions) in which the boundary line L1 may exist are indicated as percentages. If the pixel (i, j) of the tomographic image $B_k$ is determined, the probability of existence of the boundary line $L_1$ at the position of the pixel can be obtained from the existence probability image $H_{ILM}$ as a digital value corresponding to the percentage. FIG. 7 illustrates the pixel regions which are partitioned by the probability at every 25%. The percentage with which the pixel regions are partitioned by the probability is determined in accordance with the accuracy to be obtained, but practically the pixel regions are partitioned at a finer percentage of probability than illustrated in FIG. 7.

FIG. 7 illustrates that the existence probability image storage unit 26 stores ten existence probability images for respective layers of the tomographic image $B_k$. In an embodiment, however, also for tomographic images $B_N$ other than the tomographic image $B_K$ which constitute a volume image, the existence probability images may be stored for respective layers of each tomographic image. In another embodiment, one existence probability image may be stored in a shared manner for all of the images $B_1$ to $B_N$. In still another embodiment, the existence probability images may be those in which the probability is uniform in the X direction, but in the Z direction, monotonically increases or decreases in a continuous manner. In an embodiment, each existence probability image stored in the existence probability image storage unit 26 is mapped and, when the extracted boundary line is modified, the existence probability image which contributes to the extraction can also be modified accordingly. This allows sequential learning.

The existence probability image storage unit 26 can be an external storage unit rather than being provided in the image processing apparatus 20. For example, the existence probability image storage unit 26 may be provided in a server connected via the Internet.

Description herein is directed to an example in which the boundary line L1 of the internal limiting membrane (ILM) is extracted first among the boundary lines of the tomographic image $B_k$. Accordingly, the input image B and the existence probability image ILM(L1) which is determined by the boundary line L1 are read out from the existence probability image storage unit 26. The read-out existence probability image is illustrated as $H_{ILM}$ in the upper part of FIG. 5.

Subsequently, the boundary line candidate image creating means 31 of the image processing unit 30 is used to detect edges in the input image B and create a boundary line candidate image (step S3). For this edge detection, for example, a known Canny edge detection method is used. Edges extracted by the Canny edge detection method are thin edges. When a threshold is appropriately set, such as by setting a high threshold for a high-contrast region, the boundary line candidate image can be created which comprises a plurality of thin lines to be boundary line candidates in the input image B. This boundary line candidate image is an image of m×n pixels that has a value indicative of information on the presence or absence of an edge in the input image B as a digital value at a pixel position corresponding to each pixel (i, j). The boundary line candidate image is illustrated as $E_{ILM}$ in FIG. 5.

Subsequently, the luminance value-differentiated image creating means 32 is used to differentiate the luminance value of the input image B in the Z direction and create a luminance value-differentiated image (step S4). Differentiating the luminance value is calculating the luminance gradient in the Z direction. The luminance gradient is calculated, for example, using a differential filter such as a known Sobel filter. The luminance value-differentiated image is an image of m×n pixels that has a value indicative of the luminance gradient of the input image B as a digital value at a pixel position corresponding to each pixel (i, j). The luminance value-differentiated image is illustrated as $G_{ILM}$ in FIG. 5. Differentiation of the bright value allows detection of the luminance gradient of a retinal layer. The luminance value-differentiated image can therefore complement the edge information of the boundary line candidate image, such as when the information is missing or insufficient.

Subsequently, a weighting coefficient $W_{ILM}$ set for the luminance value-differentiated image is read out from the weighting coefficient storage unit 27 (step S4'). The weighting coefficient $W_{ILM}$ is used for the boundary line ILM to be obtained.

Further, an image in which the input image B is shifted in the vertical direction by a desired number of pixels is created as a luminance value information image B' (step S5), and a weighting coefficient $Q_{ILM}$ for ILM set for the luminance value information image B' is read out from the weighting coefficient storage unit 27 (step S5'). The moving amount and moving direction in the vertical direction can be appropriately changed in accordance with the boundary line to be obtained, but in an example for the case of ILM, the input image B is moved upward by 5 pixels. That is, it is preferred to determine the moving direction and the shift amount such that the luminance information overlaps the boundary line to be obtained.

Subsequently, the evaluation score image creating means 33 is used to calculate and create an evaluation score image $C_{ILM}$ on the basis of the following equation (step S6). The evaluation score image $C_{ILM}$ is calculated and created on the basis of the boundary line candidate image $E_{ILM}$, the existence probability image $H_{ILM}$, the luminance value-differentiated image $G_{ILM}$, the weighting coefficient $W_{ILM}$ set for the luminance value-differentiated image, the luminance value information image B', and the weighting coefficient $Q_{ILM}$ set for the luminance value information image.

$$C_{ILM} = E_{ILM} \times H_{ILM} + W_{ILM} \times G_{ILM} + Q_{ILM} \times B'$$

FIG. 6 illustrates a process of creating the evaluation score image $C_{ILM}$. The evaluation score image $C_{ILM}$ is formed by calculation (addition) of a boundary line position probability image, the luminance value-differentiated image $G_{ILM}$ weighted with the weighting coefficient $W_{ILM}$, and the luminance value information image B' weighted with the weighting coefficient $Q_{ILM}$. The boundary line position probability image represents two-dimensional information that includes boundary line positions obtained by calculation (multiplication) of the boundary line candidate image $E_{ILM}$ and the existence probability image $H_{ILM}$ and their existence probability. Whether the extraction of a boundary line to be extracted is easy depends on which is considered important among the edge elements, luminance value-differentiated elements, and luminance value information. To deal with this situation, the weighting coefficients $W_{ILM}$ and $Q_{ILM}$ can be set at appropriate values thereby to allow more satisfactory extraction in any case, that is, a case in which edges are considered important for extraction, a case in which luminance value differentiation is considered important for extraction, or a case in which luminance value information is considered important for extraction. The evaluation score image $C_{ILM}$ is calculated in terms of each pixel (i, j) of the boundary line candidate image EITA, the existence probability image $H_{ILM}$, and the luminance value-differentiated image $G_{ILM}$. The evaluation score image $C_{ILM}$ is therefore an image comprising m×n pixels that has a calculated value obtained by the above-described equation at a pixel position corresponding to each pixel (i, j). Each image in FIG. 6 is actually in a complicated shape and difficult to illustrate, so the outline thereof is schematically illustrated.

Each pixel (i, j) of the evaluation score image $C_{ILM}$ is scored as a digital value and, therefore, a route search is performed using dynamic programming, for example, to search for a route having the highest total score and extract the boundary line of ILM.

FIG. 8 illustrates an example of the route search. For example, the search range is set as a range of dashed lines that are illustrated in the top and bottom of the figure. Assume that the pixel line associated with the pixel position of i=1 and extending in the Z direction is a first pixel line P1. For pixels in the next pixel line P2, a pixel having the highest evaluation score is searched from among pixels in the vicinity of P1 and the position of the pixel is stored. A value obtained by adding the evaluation score of that pixel to each pixel of P2 is updated as the evaluation score of each pixel of P2. Subsequently, i is incremented and the process is repeated sequentially for pixel lines P3, ..., Pm. Thereafter, with the pixel having the largest evaluation score in the pixel line Pm as the starting point, i is decremented in turn and the stored pixel positions are traced in the order of decrement of i thereby to extract a route illustrated by a bold dashed line, which has the highest sum, as the boundary line.

In FIG. 8, thin curved lines are those obtained by calculation of the edges $E_{ILM}$ detected in the process of step S3 of FIG. 4 and the existence probability $H_{ILM}$ of the boundary line L to be extracted while a horizontally-long image having a wide width is the luminance value-differentiated image $G_{ILM}$ obtained in the process of step S4 of FIG. 4. It can be understood that the boundary line L to be extracted passes through a region having luminance gradient because the evaluation score is high within such a region. If necessary, the starting point is changed to obtain the sum for all the routes, among which a route having the highest score is extracted as the boundary line L1 in the internal limiting membrane (ILM) (step S7).

As will be understood, the route search is started from the pixel line $P_1$ in FIG. 8, but may also be started from the final pixel line $P_m$ (i=m).

As illustrated in the lower part of FIG. 6, the extracted boundary line L1 is superimposed on the input image B and displayed as a resultant image $R_{ILM}$ on the display unit 24 (step S8).

Subsequently, a determination is made as to whether all boundary lines have been extracted (step S9). If there is a boundary line that has not been extracted, the routine returns to step S2, while if all the boundary lines have been extracted, the process is ended.

As described above, in the present embodiment, the evaluation score image is formed through obtaining the positional information of the input image using the boundary line candidate image and the existence probability image, obtaining the luminance value information of the input image using the luminance value-differentiated image, and combining the positional information and the luminance value information which is weighted with an appropriate weighting coefficient. Among the pixels of the evaluation score image, a pixel in which the boundary line to be extracted exists has a high evaluation score due to the calculation using the existence probability image. Thus, the accuracy in extraction of the boundary line can be remarkably improved because the boundary line is determined by searching for such pixels having high evaluation scores.

The weighting coefficient applied to the luminance value-differentiated image can be omitted depending on the boundary line to be extracted. When extracting a plurality of boundary lines, the luminance gradient information is weighted in accordance with the boundary lines to be extracted, thereby to allow extraction of boundary lines having difference characteristics with a high degree of accuracy.

When the above-described boundary line extracted in step S7 is superimposed on the input image and displayed but the extracted boundary line is misaligned with the original boundary line, the user can modify the boundary line position, as will be described later. In this case, in accordance with the modification, the existence probability image for the boundary line stored in the existence probability image storage unit 26 can also be modified for learning.

When the weighting coefficient applied to the luminance value-differentiated image in the boundary line extraction process is modified, the boundary line can be more satisfactorily extracted. In such a case, in accordance with the modification of the weighting coefficient, the weighting coefficient for the boundary line stored in the weighting coefficient storage unit 27 may also be modified for learning.

<Extraction of a plurality of Boundary Lines>

As illustrated in step S9 of FIG. 4, when extracting a plurality of boundary lines from the input image, already extracted boundary lines can be utilized to effectively extract other boundary lines. The embodiment will be described below with reference to FIG. 9.

Among the boundary lines, the boundary line of the internal limiting membrane ILM(L1) at the uppermost end and the boundary line of the retinal pigment epithelium RPE(L10) at the lowermost end represent boundaries at which the luminance change is large, and are thus easy to extract. These boundary lines are therefore extracted first, and the extracted boundary lines are utilized to limit and/or set the search range to extract other boundary lines.

In FIG. 9, the edge detection process as described in step S3 of FIG. 4 is performed for each layer in the input image B to create the boundary line candidate images $E_{ILM}$, $E_{NFL/GCL}$, $E_{GCL/IPL}$, . . . for respective layers (step T1).

Subsequently, the luminance value differentiation is performed for each layer in the input image B to extract the luminance gradient (process in step S4 of FIG. 4), and the luminance value-differentiated images $G_{ILM}$, $G_{NFL/GCL}$, $G_{GCL/IPL}$, . . . for respective layers are created (step T2).

After such processing, the existence probability images $H_{ILM}$, $H_{NFL/GCL}$, $H_{GCL/IPL}$, . . . for respective layers, the weighting coefficients $W_{ILM}$, $W_{NFL/GCL}$, $W_{GCL/IPL}$, . . . set for the luminance value-differentiated images, and the weighting coefficients $Q_{ILM}$, $Q_{NFL/GCL}$, $Q_{GCL/IPL}$, . . . set for the luminance value information are read out from the existence probability image storage unit 26 and the weighting coefficient storage unit 27, and the process as described in step S6 of FIG. 4 is performed to create the evaluation score images for respective layers.

The uppermost ILM represents a boundary at which the luminance change is large, so the ILM is selected first in the order of extraction. The search range is set for the entire input image, and a route having the highest total score of the evaluation score $E_{ILM} \times H_{ILM} + W_{ILM} \times G_{ILM} + Q_{ILM} \times B'$ as a parameter is searched and extracted as the boundary line L1 of ILM (step T3). The process of extracting the boundary line L1 for ILM corresponds to the process described with reference to FIGS. 5, 6, and 8.

Then, the lowermost RPE is selected. In the same manner as the above, the search range is set for the entire input image, and a route having the highest total score of a parameter $E_{RPE} \times H_{RPE} + W_{RPE} \times G_{RPE} + Q_{RPE} \times B'$ is searched. The route determined to have the highest total score as a result of the search is extracted as the boundary line L10 of RPE (step T4). In an alternative embodiment, extraction of the boundary line L10 of RPE may be performed first and followed by extraction of the boundary line L1 of ILM.

Subsequently, the search range is set as a range of the already extracted boundary lines ILM(L1) to RPE(L10), and a route having the highest total score of a parameter $E_{IS/OS} \times H_{IS/OS} + W_{IS/OS} \times G_{IS/OS} + Q_{IS/OS} \times B'$ is searched and extracted as the boundary line L8 of IS/OS (step T5).

Subsequently, the search range is set as a range of the already extracted boundary lines ILM(L1) to IS/OS(L8), and a route having the highest total score of a parameter $E_{OPL/ONL} \times H_{OPL/ONL} + W_{OPL/ONL} \times G_{OPL/ONL} + Q_{OPL/ONL} \times B'$ is searched and extracted as the boundary line L6 of OPL/ONL (step T6). In addition, the search range is set as a range of the already extracted boundary lines IS/OS(L8) to RPE (L10), and a route having the highest total score of a parameter $E_{OS/RPE} \times H_{OS/RPE} + W_{OS/RPE} \times G_{OS/RPE} + Q_{OS/RPE} \times B'$ is searched and extracted as the boundary line L9 of OS/RPE (step T7).

Similarly, the search range is set as a range of the already extracted boundary lines ILM(L1) to OPL/ONL(L6), and a route having the highest total score of a parameter $E_{NFL/GCL} \times H_{NFL/GCL} + W_{NFL/GCL} \times G_{NFL/GCL} + Q_{NFL/GCL} \times B'$ is searched and extracted as the boundary line L2 of NFL/GCL (step T8). In addition, the search range is set as a range of the already extracted boundary lines OPL/ONL(L6) to IS/OS(L8), and a route having the highest total score of a parameter $E_{ELM} \times H_{ELM} + W_{ELM} \times G_{ELM} + Q_{ELM} \times B'$ is searched and extracted as the boundary line L7 of ELM (step T9).

Likewise, the search range is set as a range of the already extracted boundary lines NFL/GCL(L2) to OPL/ONL(L6), and a route having the highest total score of a parameter $E_{IPL/INL} \times H_{IPL/INL} + W_{IPL/INL} \times G_{IPL/INL} + Q_{IPL/INL} \times B'$ is searched and extracted as the boundary line L4 of IPL/INL (step T10). In addition, the search range is set as a range of the already extracted boundary lines NFL/GCL(L2) to IPL/INL(L4), and a route having the highest total score of a parameter $E_{GCL/IPL} \times H_{GCL/IPL} + W_{GCL/IPL} \times G_{GCL/IPL} + Q_{GCL/IPL} \times B'$ is searched and extracted as the boundary line L3 of GCL/IPL (step T11). Finally, the search range is set as a range of the already extracted boundary lines IPL/INL (L4) to OPL/ONL(L6), and a route having the highest total score of a parameter $E_{INL/OPL} \times H_{INL/OPL} + W_{INL/OPL} \times G_{INL/OPL} + Q_{INL/OPL} \times B'$ is searched and extracted as the boundary line L5 of INL/OPL (step T12). Ten boundary lines are thus extracted.

As will be apparent from the above-described processing, except the two internal limiting membrane ILM(L1) and retinal pigment epithelium RPE(L10) which are extracted first, the boundary lines are extracted by sequentially repeating similar processes, such as a process of limiting the search range on the basis of the previous extraction result to extract another boundary line, a process of limiting the search range on the basis of the previous extraction result to extract still another boundary line, and a process of limiting the search range on the basis of the previous extraction result to extract yet another boundary line.

Extraction of boundary lines which is performed sequentially in such a manner has advantages that not only a high-speed extraction process can be achieved because the search range is limited for any extraction but also the extraction is easy because the parameters (e.g. the existence probability and weighting coefficients) can be appropriately set again every time the range is changed. Moreover, as will be described later, it is possible to avoid crossing with the already extracted boundary lines or to extract a boundary line that is ambiguous or disappears, because the already extracted boundary lines can be utilized to set the search range.

Furthermore, when extracting a plurality of boundary lines, curvature correction can be performed using one or more boundary lines that are previously extracted. For example, when the boundary line of IS/OS(L8) is extracted in step T5 of FIG. 9, the input image may be corrected (in particular, the inclination may be corrected) to match the curvature of the boundary line ILM(L1) or RPE(L10) which is previously extracted, and thereafter another boundary line can be extracted. Such curvature correction can improve the accuracy in extraction of the boundary lines because the directions of edges and luminance gradient are aligned.

In the above-described process, when the user modifies a boundary line, the extraction process is performed again for boundary lines that are extracted after the modified boundary line. For example, when OPL/ONL(L6) is extracted in step T6 of FIG. 9 and the user modifies the extracted boundary line, the extraction process is performed again in the processes of steps T8, T9, T10, and T12 in which the modified boundary line is used to set the search ranges and extract boundary lines.

<Setting of Search Range>

The image processing unit 30 is provided with the search range setting means 35, which can be used to dynamically set the search range for a boundary line utilizing one or more already extracted boundary lines.

Its examples are illustrated in FIGS. 10 and 11. In a case in which an already extracted boundary line is not utilized, when the search is started from the pixel of interest I(i, j) to the left side, for example, a pixel line of (2s+1) pixel width is set as the search range which is a range of ±s centered on the left adjacent pixel (i−1, j) to the pixel of interest I(i, j), as illustrated in FIG. 10(*a*).

In contrast, when an already extracted boundary line is utilized to set the search range for a boundary line, the search range is dynamically set in accordance with the inclination of an already extracted boundary line L. As illustrated in FIG. 10(*b*), the inclination of an already extracted boundary line L refers to a degree of deviation in the Z direction between a pixel in which the already extracted boundary line L in the pixel line i is extracted and a pixel in which the already extracted boundary line L in the pixel line i−1 shifted from the pixel of the pixel line i in the X direction by one pixel width is extracted. When the inclination of the already extracted boundary line L is represented by d, the pixel line shifted by d from the left adjacent pixel (i−1, j) adjacent to the pixel of interest I (i, j) in the direction toward the already extracted boundary line is set as the search range. That is, the pixel line of (2s+1) pixel width with s+d in the direction toward the boundary line and s−d in the opposite direction is set as the search range. Similarly, other search ranges are set to match the already extracted boundary lines.

Thus, the search range is set to match the inclination of the already extracted boundary line thereby to allow highly-accurate extraction of a boundary line that is a similar curve to the already extracted boundary line.

Moreover, as illustrated in FIG. 10(*b*), the search range is set such that the upper end pixel of the search range is separated from the already extracted pixel in the pixel line by a predetermined pixel d', and the search can thereby be performed within a range that does not cross the already extracted boundary line. This can avoid crossing of the extracted boundary lines.

In some cases, as illustrated in the upper part of FIG. 11, when the already extracted boundary lines are represented by L and L' while a boundary line, located therebetween, to be extracted is represented by L", the boundary line L" may be ambiguous in the middle or discontinuous due to disappearance.

When the search range is not set to match the already extracted boundary lines, as illustrated in the left side of the figure, a pixel line having a 3-pixie length in the Z direction is set as a part of the search range so as to be centered on the left adjacent pixel (i−1, j) to the pixel of interest I (i, j) and, in a similar manner, pixel lines having a 3-pixel length are sequentially set at the left side as parts of the search range (in this case, s=1). The set final search range is a range as illustrated in the middle of the left side. Then, when the route search is performed such that the evaluation score is highest, the extracted boundary line will be a curve indicated by a dashed line as illustrated in the lower part and cross the already extracted boundary line located below. This causes a situation in which a continuous boundary line cannot be extracted.

In contrast, when the search range is set to match the already extracted boundary lines, it is possible to extract a boundary line that is ambiguous or discontinuous. This is illustrated at the right side of FIG. 11. The search range is set herein to match the extracted boundary line L. That is, as illustrated at the right side, parts of the search range to be sequentially set are arranged to match the already extracted boundary line L so as not to cross the pixels of the already extracted boundary lines L and L' and so as to include a pixel I' that connects to the ambiguous or disappearing portion. The set final search range is therefore a range as illustrated in the middle at the right side. When the route search is performed, the extracted boundary line will be a curve as indicated by a dashed line in the lower part. It is thus possible to extract a boundary line connected to a disappearing portion or an ambiguous portion. In this case, the extracted boundary line can be avoided from crossing the already extracted boundary lines L and L' because the search range is set so as not to cross the pixels of the already extracted boundary lines.

In the examples illustrated in FIGS. 10 and 11, the search is performed from the right to the left. In an alternative example, the search may be performed in the reverse direction.

Thus, the already extracted boundary lines are utilized to appropriately set the search range and it is thereby possible to extract an ambiguous boundary line or a boundary line that partially disappears, without crossing the already extracted boundary lines.

<Setting of Control Points>

As illustrated in FIGS. 12 and 13, control points can be set on each boundary line extracted via the process as described above.

For example, the user specifies one point on the boundary line using the mouse or operation pen of the operation unit 25 and also specifies a pixel interval D. The control unit 21 identifies a pixel on the specified boundary line, and the control point setting means 36 is used to set control points centered on the identified pixel in the right and left of the X direction, at pixel positions at which the D×n-th (n=1, 2, . . . ) pixel line and the boundary line cross each other. In an alternative embodiment, the control unit 21 may set the control points at given X-direction positions on the specified boundary line.

The control points thus set are displayed on the display unit 24. For example, as illustrated in the lower left diagram of FIG. 12, control points indicated by black circles are set at a 5-pixel interval on the retinal pigment epithelium RPE(L10) at the lowermost end. In addition or alternatively, as illustrated in the lower middle diagram, control points are set at a 10-pixel interval. In addition or alternatively, as illustrated in the lower right diagram, control points are set at a 50-pixel interval.

In the boundary line extracted using the method illustrated in FIG. 6, the pixel interval is narrow (1-pixel interval), so that fine irregularities may occur and a smooth curve may not be obtained even though the boundary line is originally smooth. However, fortunately, the boundary line can be approximated to a smooth curve that is easy to subjectively perceive, through setting the control points on the boundary line at a wider pixel interval, such as a 5-pixel interval and 10-pixel interval, as described above, connecting the set control points using a spline curve, for example, and employing it as the boundary line.

A narrowed control point interval allows faithful representation of the extracted result, but modification of the boundary line takes time because the number of control points increases. In addition, when the control point interval is narrowed, fine irregularities may occur even on a smooth boundary line and a smooth curve cannot be obtained. Accordingly, the degree of pixel interval at which the control points are set may be set by the user in accordance with the features of the boundary line to be extracted or in accordance with the degree of modification necessary for the extracted boundary line.

For example, the upper diagram of FIG. 13 illustrates an example in which control points are set on the extracted boundary line NFL/GCL(L2) at a narrow pixel interval and the control points are connected by a spline curve to form a boundary line, and the middle part illustrates an example in which control points are set at a wide pixel interval to form a boundary line.

When the control point interval is increased, the number of control points to be modified is reduced, and the modification time can be shortened. For example, as illustrated in the lower part of FIG. 13, the extracted boundary line can be modified by moving a control point Q to Q'. However, if similar modification is performed with a narrowed control point interval as illustrated in the upper diagram of FIG. 13, it is necessary to move a plurality of control points and the modification takes time. In other words, there are trade-off relationships among the accuracy of the extraction result, the time and effort for the modification, and the smoothness of appearance, and this balance can come close to the user's requirement when the user specifies the control point interval.

When control points are set on a boundary line at a given pixel interval as described above, one or more set control points may be removed and the remaining control points can be connected by a spline curve. Alternatively, one or more control points may be added to a space or spaces between the set control points and these control points can be connected by a spline curve to form a boundary line. Thus, the control points can be removed, added, or moved thereby to extract a smoother or faithful boundary line.

As described above, the lower part of FIG. 13 illustrates a state in which the control point Q is moved to Q' to modify the extracted boundary. Such an operation can move not only one control point but also a plurality of control points. Also as described above, one or more control points can be added or removed. When the control points are moved, added, and/or removed in such a manner, the boundary line extracting means 34 may perform a route search again for one or all of the boundary lines to retry extraction of a boundary line. In this operation, in order that the route search is performed to pass through a moved control point or added control point, a pixel in which the moved or added control point is positioned may be given a high evaluation score. In addition or alternatively, in order that the route search is performed so as not to pass through a removed control point, a pixel in which the removed control point is positioned may be given a low evaluation score or may not be given an evaluation score.

In a case in which the route search is performed again for a plurality of boundary lines, in order to prevent the phenomenon of crossing of the boundary lines, when a control point $Q(x, z)$ on a boundary line A moves to $Q'(x, z')$, the following measures can be taken at the time of re-detection of a boundary line B. For example, as illustrated in FIG. 14, when the control point $Q(x, z)$ on the boundary line A moves to $Q'(x, z')$ in the −Z direction across the boundary line B, a half-line region having the end point of $Q'(x, z')$ and extending in the +Z direction may be excluded from the search range at the time of detection of the boundary line B. Similarly, when the control point $Q(x, z)$ on the boundary line A moves to $Q'(x, z')$ in the +Z direction across the boundary line B, a half-line region having the end point of $Q'(x, z')$ and extending in the −Z direction may be excluded from the search range at the time of detection of the boundary line B. As illustrated in FIG. 15, when the control point $Q(x, z)$ on the boundary line A moves to $Q'(x, z')$ in the +Z direction without crossing the boundary line B, a half-line region having the end point of $Q'(x, z')$ may be excluded from the search range at the time of detection of the boundary line B. This half-line region is parallel to the Z axis and does not cross the boundary line B. The same applies to a case in which the control point $Q(x, z)$ on the boundary line A moves in the −Z direction without crossing the boundary line B.

When the boundary line is modified, as described above, in accordance with the modification, the existence probability image for the boundary line stored in the existence probability image storage unit 26 can also be modified for learning of the existence probability image.

DESCRIPTION OF REFERENCE NUMERALS

10 Tomography apparatus
20 Image processing apparatus
21 Control unit
22 Tomographic image forming unit
23 Storage unit
24 Display unit
25 Operation unit
26 Existence probability image storage unit
27 Weighting coefficient storage unit
30 Image processing unit
31 Boundary line candidate image creating means
32 Luminance value-differentiated image creating means
33 Evaluation score image creating means
34 Boundary line extracting means
35 Search range setting means
36 Control point setting means

The invention claimed is:

1. An image processing apparatus comprising:
   boundary line candidate image creating means for creating a boundary line candidate image using an input image obtained by capturing an optical tomographic image of an ocular fundus composed of a plurality of retinal layers, the boundary line candidate image representing edges of the retinal layers detected from the input image as boundary line candidates;
   luminance value-differentiated image creating means for differentiating a luminance value of the input image to create a luminance value-differentiated image, the luminance value-differentiated image representing luminance gradient of the retinal layers; and
   boundary line extracting means for performing a route search to extract a boundary line, the route search being performed on a basis of a boundary line position probability image and the luminance value-differentiated image, the boundary line position probability image representing a boundary line position and created from the boundary line candidate image and an existence probability image, the existence probability image representing the probability of existence of the boundary line to be extracted as a digital value at a pixel position corresponding to each pixel of the image.

2. The image processing apparatus as recited in claim 1, further comprising
   luminance value information image creating means for creating a luminance value information image in which the input image is shifted in a vertical direction by a desired number of pixels.

3. The image processing apparatus as recited in claim 1, wherein the luminance value-differentiated image is weighted with a first weighting coefficient in accordance with the boundary line to be extracted.

4. The image processing apparatus as recited in claim 2, wherein the luminance value information image is weighted with a second weighting coefficient in accordance with the boundary line to be extracted.

5. The image processing apparatus as recited in claim 2, wherein
   the luminance value-differentiated image is weighted with a first weighting coefficient in accordance with the boundary line to be extracted, and
   the luminance value information image is weighted with a second weighting coefficient in accordance with the boundary line to be extracted.

6. The image processing apparatus as recited in claim 1, wherein the existence probability image is read out from an existence probability image storage unit in accordance with the boundary line to be extracted, wherein the existence probability image storage unit stores the existence probability image for each boundary line of the retinal layers.

7. The image processing apparatus as recited in claim 3, wherein the first weighting coefficient is read out from a weighting coefficient storage unit in accordance with the boundary line to be extracted, wherein the weighting coefficient storage unit stores a weighting coefficient for each boundary line of the retinal layers.

8. The image processing apparatus as recited in claim 4, wherein the second weighting coefficient is read out from a weighting coefficient storage unit in accordance with the boundary line to be extracted, wherein the weighting coefficient storage unit stores a weighting coefficient for each boundary line of the retinal layers.

9. The image processing apparatus as recited in claim 3, wherein an evaluation score image is created on a basis of the boundary line position probability image, the luminance value-differentiated image, and the first weighting coefficient, wherein the boundary line position probability image represents the boundary line position and is created from the boundary line candidate image and the existence probability image which represents existence of the boundary line to be extracted, wherein the boundary line extracting means searches for a route having a highest total evaluation score from the created evaluation score image and extracts the route having the highest total evaluation score as the boundary line.

10. The image processing apparatus as recited in claim 5, wherein an evaluation score image is created on a basis of the boundary line position probability image, the luminance value-differentiated image, the first weighting coefficient, the luminance value information image, and the second weighting coefficient, wherein the boundary line position probability image represents the boundary line position and is created from the boundary line candidate image and the existence probability image which represents existence of the boundary line to be extracted, wherein the boundary line extracting means searches for a route having a highest total evaluation score from the created evaluation score image and extracts the route having the highest total evaluation score as the boundary line.

11. The image processing apparatus as recited in claim 6, wherein, when the extracted boundary line is modified, the existence probability image for the boundary line stored in the existence probability image storage unit is modified.

12. The image processing apparatus as recited in claim 3, wherein, when the first weighting coefficient is modified, the first weighting coefficient stored in the weighting coefficient storage unit is modified.

13. The image processing apparatus as recited in claim 4, wherein, when the second weighting coefficient is modified, the second weighting coefficient stored in the weighting coefficient storage unit is modified.

14. An image processing method comprising:
    a step of creating a boundary line candidate image using an input image obtained by capturing an optical tomographic image of an occular fundus composed of a plurality of retinal layers, the boundary line candidate image representing edges of the retinal layers detected from the input image as boundary line candidates;
    a step of differentiating a luminance value of the input image to create a luminance value-differentiated image, the luminance value-differentiated image representing luminance gradient of the retinal layers; and
    a step of performing a route search to extract a boundary line, the route search being performed on a basis of a boundary line position probability image and the luminance value-differentiated image, the boundary line position probability image representing a boundary line position and created from the boundary line candidate image and an existence probability image, the existence probability image representing the probability of existence of the boundary line to be extracted as a digital value at a pixel position corresponding to each pixel of the image.

15. The image processing method as recited in claim 14, further comprising
    a step of creating a luminance value information image in which the input image is shifted in a vertical direction by a desired number of pixels.

16. The image processing method as recited in claim 14, wherein the luminance value-differentiated image is weighted with a first weighting coefficient in accordance with the boundary line to be extracted.

17. The image processing method as recited in claim 15, wherein the luminance value information image is weighted with a second weighting coefficient in accordance with the boundary line to be extracted.

18. The image processing method as recited in claim 15, wherein
the luminance value-differentiated image is weighted with a first weighting coefficient in accordance with the boundary line to be extracted, and
the luminance value information image is weighted with a second weighting coefficient in accordance with the boundary line to be extracted.

19. The image processing method as recited in claim 16, wherein an evaluation score image is created on a basis of the boundary line position probability image, the luminance value-differentiated image, and the first weighting coefficient, wherein the boundary line position probability image represents the boundary line position and is created from the boundary line candidate image and the existence probability image which represents existence of the boundary line to be extracted, wherein a route having a highest total evaluation score is searched from the created evaluation score image and extracted as the boundary line.

20. The image processing method as recited in claim 18, wherein an evaluation score image is created on a basis of the boundary line position probability image, the luminance value-differentiated image, the first weighting coefficient, the luminance value information image, and the second weighting coefficient, wherein the boundary line position probability image represents the boundary line position and is created from the boundary line candidate image and the existence probability image which represents existence of the boundary line to be extracted, wherein a route having a highest total evaluation score is searched from the created evaluation score image and extracted as the boundary line.

21. A non-transitory computer readable storage medium that stores an image processing program that causes a computer to serve as the image processing apparatus as recited in claim 1.

* * * * *